US011587140B2

United States Patent
Leifer et al.

(10) Patent No.: US 11,587,140 B2
(45) Date of Patent: Feb. 21, 2023

(54) METHODS FOR IMPROVING FOOD-RELATED PERSONALIZATION

(71) Applicant: KRAFT FOODS GROUP BRANDS LLC, Chicago, IL (US)

(72) Inventors: Tjarko Leifer, San Francisco, CA (US); Erik Andrejko, San Francisco, CA (US); Sivan Aldor-Noiman, San Francisco, CA (US)

(73) Assignee: Kraft Foods Group Brands LLC, Chicago, IL (US)

( * ) Notice: Subject to any disclaimer, the term of this patent is extended or adjusted under 35 U.S.C. 154(b) by 9 days.

(21) Appl. No.: 16/803,550

(22) Filed: Feb. 27, 2020

(65) Prior Publication Data

US 2020/0265497 A1  Aug. 20, 2020

Related U.S. Application Data

(63) Continuation of application No. 16/258,325, filed on Jan. 25, 2019, now Pat. No. 10,776,856.

(Continued)

(51) Int. Cl.
*G06Q 30/06* (2012.01)
*G16H 20/60* (2018.01)
(Continued)

(52) U.S. Cl.
CPC ..... *G06Q 30/0631* (2013.01); *G06F 16/9035* (2019.01); *G06F 16/90324* (2019.01);
(Continued)

(58) Field of Classification Search
CPC .......... G06Q 30/0631; G06Q 30/0621; G06Q 30/0633; G06Q 30/0601–0643;
(Continued)

(56) References Cited

U.S. PATENT DOCUMENTS 5,212,766 A   5/1993  Arima
6,370,513 B1 *  4/2002  Kolawa ................. G06Q 30/02
                                                                    705/15
(Continued)

FOREIGN PATENT DOCUMENTS

KR   20180060257 A   6/2018
WO     2008091281 A2   7/2008
(Continued)

OTHER PUBLICATIONS

Khoury, Rita. Food Logging Is Old School: 'Eat This Much' Plans Your Meals Ahead Based On Dietary Preferences And Fitness Goals. Apr. 12, 2016. (Year: 2016).*

(Continued)

*Primary Examiner* — Allison G Wood
(74) *Attorney, Agent, or Firm* — Fitch, Even, Tabin & Flannery LLP

(57) ABSTRACT

Systems and methods for improving food-related personalization for a user including generating a recipe database including a set of recipe data structures; deriving a recipe vector representation of the recipe data structures; determining a set of user food preferences; extracting a set of recipe vector constraints from the set of user food preferences; determining a personalized food plan for the user, including automatically selecting a subset of the set of recipe data structures associated with recipe vector representations that satisfy the set of recipe vector constraints; determining fulfillment parameters for grocery items associated with the personalized food plan; and automatically facilitating fulfillment of grocery items associated with the personalized food plan based on the fulfillment parameters.

16 Claims, 2 Drawing Sheets

Related U.S. Application Data

(60) Provisional application No. 62/621,771, filed on Jan. 25, 2018.

(51) Int. Cl.

| | |
|---|---|
| *G06N 3/08* | (2006.01) |
| *G06Q 30/0601* | (2023.01) |
| *G06F 16/9032* | (2019.01) |
| *G06N 5/04* | (2023.01) |
| *G06N 20/10* | (2019.01) |
| *G06F 16/9035* | (2019.01) |

(52) U.S. Cl.
CPC .............. *G06N 3/08* (2013.01); *G06N 5/04* (2013.01); *G06N 20/10* (2019.01); *G06Q 30/0633* (2013.01); *G16H 20/60* (2018.01)

(58) Field of Classification Search
CPC .......... G06Q 30/0269; G06F 16/90324; G06F 16/9035; G06N 3/08; G06N 3/0472; G06N 3/0454; G06N 3/084; G06N 3/088; G06N 5/04; G06N 5/003; G06N 5/025; G06N 20/10; G06N 20/20; G06N 7/005; G16H 20/60
USPC ........ 705/26.1–27.2, 26.7, 26.64, 26.61, 26.8
See application file for complete search history.

(56) References Cited

U.S. PATENT DOCUMENTS

| | | | |
|---|---|---|---|
| 8,276,505 B2 | 10/2012 | Buehler | |
| 8,429,026 B1 | 4/2013 | Kolawa et al. | |
| 8,849,805 B2 | 9/2014 | Osaki | |
| 9,129,277 B2 | 9/2015 | Macintosh | |
| 9,212,996 B2 | 12/2015 | Watson | |
| 10,776,856 B2 | 9/2020 | Leifer et al. | |
| 2008/0086374 A1 | 4/2008 | Aitken | |
| 2009/0037288 A1 | 2/2009 | Christensen | |
| 2009/0075242 A1 | 3/2009 | Schwarzberg | |
| 2009/0236333 A1 | 9/2009 | Ben-Shmuel | |
| 2009/0254541 A1 | 10/2009 | Kolawa | |
| 2013/0224694 A1 | 8/2013 | Moore et al. | |
| 2013/0269297 A1 | 10/2013 | Minvielle | |
| 2013/0280681 A1 | 10/2013 | Narayan | |
| 2014/0052722 A1 | 2/2014 | Bertsimas | |
| 2015/0066909 A1 | 3/2015 | Uchida et al. | |
| 2015/0109451 A1 | 4/2015 | Dhankhar | |
| 2015/0170543 A1* | 6/2015 | Shahar ............... G09B 19/0092 434/127 |
| 2015/0287056 A1 | 10/2015 | Osogami | |
| 2015/0290795 A1 | 10/2015 | Oleynik | |
| 2016/0073886 A1* | 3/2016 | Connor ................ A61B 5/681 600/407 |
| 2016/0081515 A1* | 3/2016 | Aboujassoum .... G09B 19/0092 426/231 |
| 2016/0180739 A1 | 6/2016 | Minvielle | |
| 2016/0232625 A1 | 8/2016 | Akutagawa et al. | |
| 2016/0275397 A1 | 9/2016 | Neil | |
| 2016/0350834 A1 | 12/2016 | Wilson | |
| 2017/0053551 A1 | 2/2017 | Prisk | |
| 2017/0316488 A1* | 11/2017 | Kremen ............. G09B 19/0092 |
| 2017/0320655 A1 | 11/2017 | Minvielle | |
| 2017/0372197 A1* | 12/2017 | Baughman ............. A23L 33/30 |
| 2018/0033074 A1 | 2/2018 | Grueneberg | |
| 2018/0137249 A1 | 5/2018 | Eggebraaten | |
| 2018/0203978 A1 | 7/2018 | Basu | |
| 2018/0308143 A1* | 10/2018 | Chan .................. G06Q 30/0643 |
| 2018/0314804 A1 | 11/2018 | Gorre | |
| 2019/0050624 A1 | 2/2019 | Chai | |
| 2019/0073581 A1 | 3/2019 | Chen | |
| 2019/0147340 A1 | 5/2019 | Zhang | |
| 2019/0171707 A1* | 6/2019 | Rapaport ................. G06N 3/08 |
| 2019/0197466 A1 | 6/2019 | Hand et al. | |
| 2019/0215424 A1 | 7/2019 | Adato et al. | |
| 2019/0228855 A1 | 7/2019 | Leifer | |
| 2019/0228856 A1 | 7/2019 | Leifer | |
| 2019/0236362 A1 | 8/2019 | Srivastava et al. | |
| 2020/0303055 A1 | 9/2020 | Leifer | |

FOREIGN PATENT DOCUMENTS

| | | |
|---|---|---|
| WO | 2017075498 A1 | 5/2017 |
| WO | 2018198100 A1 | 11/2018 |

OTHER PUBLICATIONS

Instacart, PlateJoy partner to deliver recommended groceries to dieters. Lora Kolodny. May 3, 2016. (May 3, 2016). Published by TechCrunch. (Year: 2016).

"Examining the Use of Neural Networks for Feature Extraction: A Comparative Analysis using Deep Learning, Support Vector Machines, and K-Nearest Neighbor Classifiers", Notley, Stephen et al. , Department of Computer Science, Rensselaer Polytechnic Institute, Troy NY, Jun. 12, 2018.

International Search Report and Written Opinion of the ISA, dated Mar. 26, 2019, for application No. PCT/US19/015267.

Charpiat, Guillaume et al. "Input Similarity from the Neural Network Perspective" 33rd Conference on Neural Information Processing Systems, (NeurIPS 2019), Vancouver, Canada.

"WiFIRE® Controller: Creating Custom Cook Cycles | Trager Grills", https://www.youtube.com/watch?v=jyx3fow_cpc, Mar. 29, 2017.

Bojinov, Hristo; "Deep Learning in the Connected Kitchen or Launching a Computer Vision program in a new vertical"; Innit; dated Jun. 8, 2017; 28 pages.

Evangelista, Benny "SF startups recipe for smart kitchen starts with oven"; San Francisco Chronicle; dated Sep. 4, 2016; 12 pages.

Innit: "Enjoy The Way You Eat"; Webarchive.org/web/20180107231742/ https://www.init.com; dated Jan. 7, 2018; downloaded May 31, 2022; 6 pages.

Innit; "Innit Launches App to Revolutionize The Way We Eat"; Innit Press Release; https://www.innit.com/pressreleases/innitlaunch/; dated Dec. 5, 2017; 3 pages.

Innit: "Innit Unveils Connected Food Platform"; Businesswire; dated May 19, 2016; 2 pages.

Judkis; "Recipes are dead: What the future of cooking might look like"; The Washington Post; dated Dec. 6, 2017; 8 pages.

Kontzer; "How Deep Learning Will Stir More Joy into Your Cooking"; NvidiaBlog; https://blogs.nvidia.com/blog/2017/05/11/how-deep-learning-will-stir-more-joy-into-your-cooking/; dated May 11, 2017; 3 pages.

Leifer; U.S. Appl. No. 16/900,156, filed Jun. 12, 2020.

Soares de Almeida; "Personalized Food Recommendations"; Tecnico Lisboa; Nov. 2015 (Year: 2015).

USPTO; Non-Final Office Action issued in U.S. Appl. No. 16/900,156 dated Feb. 15, 2022.

USPTO; Restriction Requirement issued in U.S. Appl. No. 16/900,156 dated Nov. 23, 2021.

* cited by examiner

METHODS FOR IMPROVING FOOD-RELATED PERSONALIZATION

CROSS REFERENCE TO RELATED APPLICATIONS

This application is a continuation application of U.S. patent application Ser. No. 16/258,325 filed 25 Jan. 2019, which claims the benefit of U.S. Provisional Application Ser. No. 62/621,771, filed 25 Jan. 2018, all of which are incorporated herein in their entirety by this reference.

TECHNICAL FIELD

This invention relates generally to the food technology field, and more specifically to a new and useful method and system for improving food-related personalization.

BACKGROUND

In the food technology field, the typical food consumer or preparer is often an amateur that lacks specialized knowledge in food science, recipe creation, and related aspects of food technology. Thus recipes, including a set of ingredients and guidelines for food preparation, are created by more experienced food preparers for dissemination to amateur food preparers and/or the public at large. However, availability of ingredients or lack thereof, ingredient cost, and/or user-specific food preferences can cause difficulty in following such recipes, given the lack of specialized knowledge on the substitutability of similar ingredients and the associated changes in the preparation guidelines on the part of the amateur food preparer or other member of the food-preparing public. Conventional approaches include simple heuristics that can be learned, but the considerations are often too complex and thus such heuristics regularly fail. Amateur food preparers can attempt to seek out detailed substitution information, but the information is often inconsistent across available sources (e.g., the Internet) and performing such a search requires some preexisting knowledge concerning what to seek out.

Thus, there is a need in the food technology field for methods and systems for improving food-related personalization to user needs. This invention provides such new and useful methods and systems.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 1:
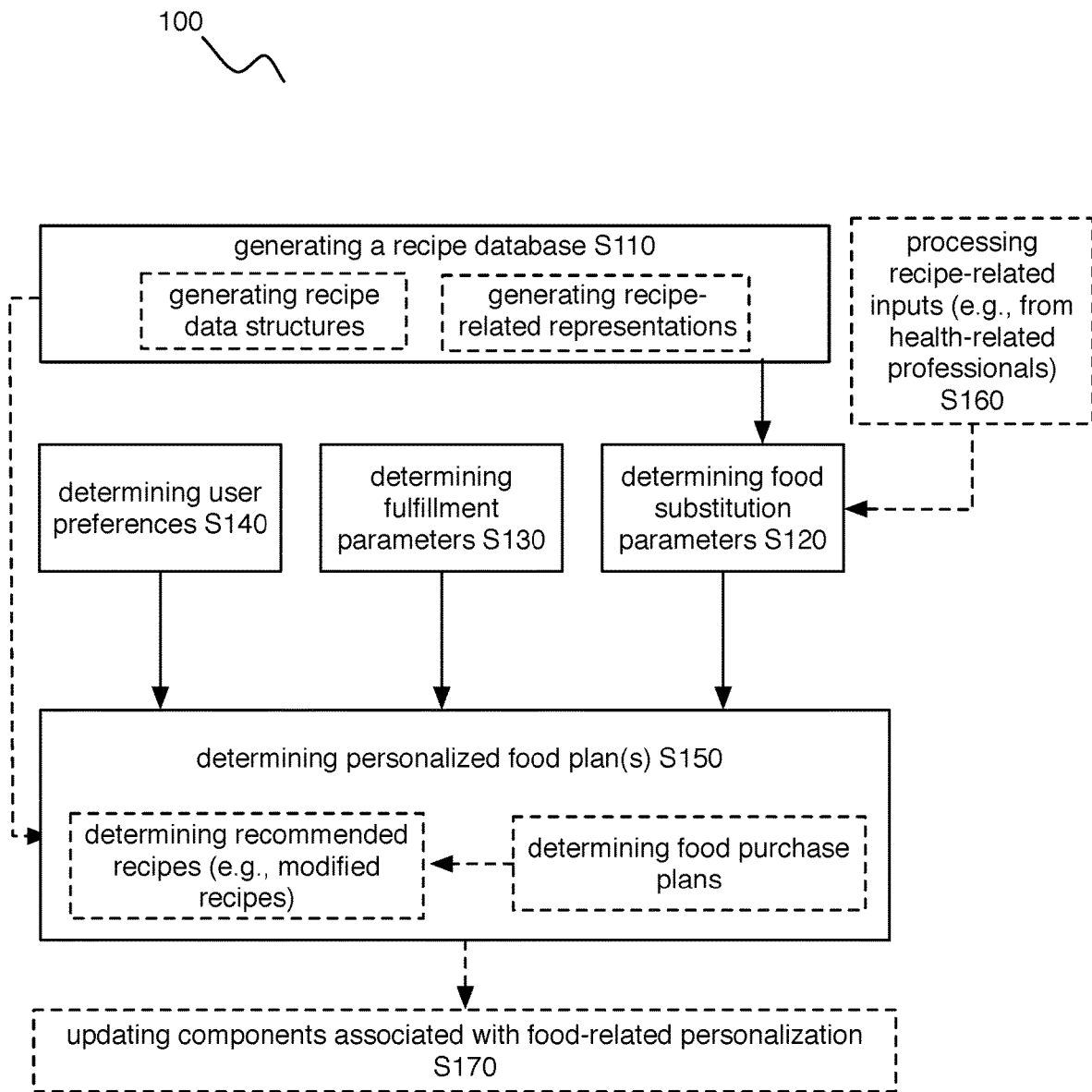
FIG. 1 is a schematic representation of variations of embodiments of the method.
Figure 2:
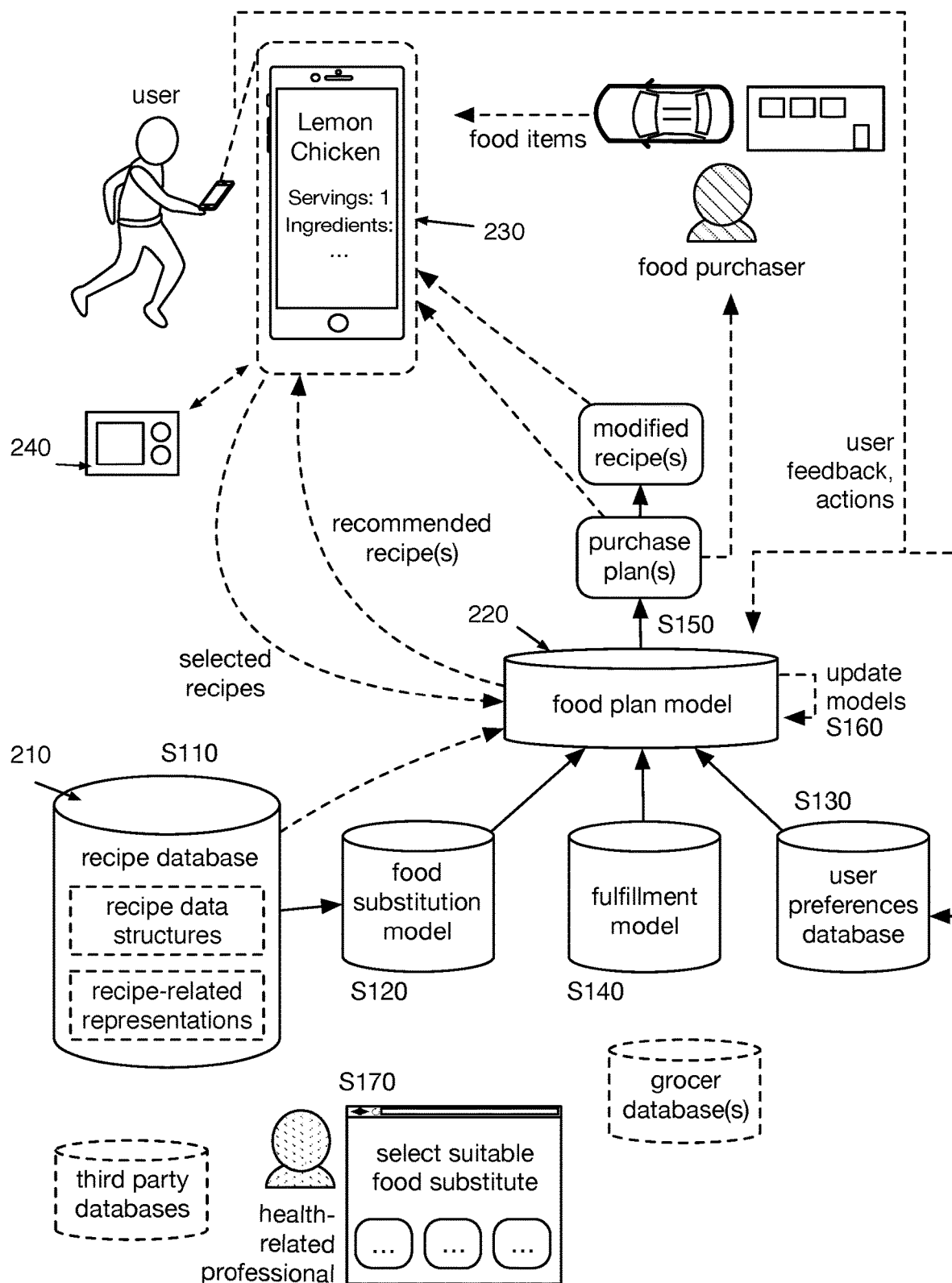
FIG. 2 is a schematic representation of variations of embodiments of the method.

As shown in FIGS. 1-2, embodiments of a method 100 for improving food-related personalization for a user can include any one or more of: generating a recipe database including at least one of recipe data structures (e.g., including preparation parameters, ingredient entities, associated characteristics, etc.) and recipe-related representations (e.g., vector representations of recipe data structures, of ingredients and/or ingredient entities, other non-vector abstractions or representations, etc.) Silo; determining food substitution parameters based on the recipe database S120; determining user food preferences associated with the food-related personalization S130; determining fulfillment parameters for grocery items associated with the food-related personalization S140; and determining one or more personalized food plans for a user based on at least one of user food preferences, fulfillment parameters, food substitution parameters, recipe-related representations, and recipe data structures, where the one or more personalized food plans can facilitate physical delivery and/or pick-up of the food items (e.g., an ingredient entity, a combination of ingredient entities, a meal, a portion of a meal, other selected food items, etc.) corresponding to the personalized food plans S150. Additionally or alternatively, embodiments of the method 100 can include: updating components associated with the food-related personalization (e.g., food substitution parameters, user food preferences, models, etc.) and/or other suitable data described herein S160; processing recipe-related inputs from one or more health-related professionals (e.g., nutritionist, dietician, food expert, chef, physical trainer, etc.) Silo.

Embodiments of the method 100 and/or system 200 can function to improve food-related personalization for a user, such as through generating food plans tailored to user food preferences (e.g., personalized food plans) and/or food substitution parameters, while satisfying various constraints (e.g., fulfillment restrictions, availability to the user due to he or she already possessing food items or ingredients, cost restrictions, etc.).

In a variation, embodiments can function to recommend food items to one or more users (e.g., in a partial fulfillment application), such as food items recommended to complement other food items (e.g., selected by the user, such as at a digital shopping cart) or satisfying ingredient requirements for a personalized recipe for the user. As such, embodiments can perform any suitable portion of the method 100 in any suitable order (e.g., determining a personalized food plan incorporating user food preferences, fulfillment parameters, and/or substitution parameters, and subsequently recommending food items corresponding to ingredient entities absent in a digital shopping cart of a user; etc.). In an example, in response to determining search intent for a user desire for scallions, portions of the method 100 can be applied for presentation of chives and/or shallots to the user in response to detecting unavailability for the scallions, based on substitution parameters (e.g., indicating substitutability of the chives for the scallions for a particular recipe when used raw; indicating substitutability of the shallots for the scallions for a particular recipe when cooked, etc.). In a related example, in response to determining search intent for a user desire for scallions, portions of the method 100 can be applied for presentation synonymous items (e.g., green onions) to the user based on substitution parameters (e.g., associated with different names for the same ingredients across different food suppliers, associated with typographical errors by the user or food supplier provider, etc.). In examples, food item recommendations can be incorporated into grocery item recommendations (e.g., to purchase at a grocer entity; etc.), meal recommendations, automated purchasing (e.g., of grocery items, meals, etc.), and/or any other suitable applications of portions of the method 100.

In another variation, embodiments can function to create recipes, such as de novo recipes, in an additional or alternative manner to modifying recipes. In another variation, embodiments can function to reduce food waste. In an example, embodiments can reduce food waste through dynamic adjusting of the amount of an ingredient entity (e.g., adjusted based on an analysis of a user's current supply of the ingredient entity inferred through historic purchasing plans, food-related device data, etc.).

Additionally or alternatively, data described herein (e.g., recipe data structures, recipe-related representations, food substitution parameters, user food preferences, fulfillment parameters, personalized food plans, recipe-related inputs, other data associated with portions of the method 100, etc.), can be associated with any suitable temporal indicators (e.g., seconds, minutes, hours, days, weeks, etc.) including one or more: temporal indicators indicating when the data was collected, determined, transmitted, received, and/or otherwise processed; temporal indicators providing context to content described by the data; changes in temporal indicators (e.g., data over time; change in data; data patterns; data trends; data extrapolation and/or other prediction; etc.); and/or any other suitable indicators related to time.

Additionally or alternatively, parameters, metrics, inputs, outputs, and/or other suitable data can be associated with value types including: scores (e.g., substitutability scores for ingredients or ingredient substitution; user food preference scores indicating a strength of the preference(s) by the user; similarity scores between types of ingredient entities; recipe matching scores indicating the degree to which user food preferences are satisfied by a given recipe; etc.), binary values (e.g., available versus unavailable in relation to food item availability; etc.), classifications (e.g., ingredient entity types; preparation levels; dietary preferences; etc.), confidence levels (e.g., associated with food item availability, substitutability, etc.), values along a spectrum, and/or any other suitable types of values. Any suitable types of data described herein can be used as inputs (e.g., for different models described herein; for portions of the method 100; etc.), generated as outputs (e.g., of models), and/or manipulated in any suitable manner for any suitable components associated with the method 100 and/or system 200.

One or more instances and/or portions of the method 100 and/or processes described herein can be performed asynchronously (e.g., sequentially), concurrently (e.g., in parallel; concurrently on different threads for parallel computing to improve system processing ability for improving food-related personalization across a plurality of users, user food preferences, grocer entities, and/or other suitable entities; etc.), in temporal relation to a trigger event (e.g., performance of a portion of the method 100), and/or in any other suitable order at any suitable time and frequency by and/or using one or more instances of the system 200, components, and/or entities described herein.

As shown in FIG. 2, embodiments of the system 200 can include a food personalization system 210 (e.g., a remote computing system configured to improve food-related personalization; etc.), databases (e.g., recipe database, food substitution database, user food preference database, fulfillment prediction database, food plan database, etc.) which can be integrated into a food plan module 220, and/or any other suitable components. Additionally or alternatively, the system 200 and/or portions of the system 200 can entirely or partially be executed by, hosted on, communicate with, and/or otherwise include: a remote computing system (e.g., a server; at least one networked computing system; stateless; stateful; etc.), a local computing system 230, one or more user devices (e.g., a mobile device; a cooking device such as a smart cooking device 240 operable to receive control instructions for cooking a personalized recipe determined by portions of the method 100; a medical device such as a health tracker; a food-related device such as a connected or smart refrigerator or freezer; etc.), and/or any suitable component. Communication by and/or between any components of the system 200 can include wireless communication (e.g., WiFi, Bluetooth, radiofrequency, etc.), wired communication, and/or any other suitable types of communication.

The components of the system 200 can be physically and/or logically integrated in any manner (e.g., with any suitable distributions of functionality across the components in relation to portions of the method 100; etc.). However, the method 100 and/or system 200 can additionally or alternatively be configured in any other suitable manner.

2.1 Generating a Recipe Database.

Block S110 can include generating a recipe database including at least one of recipe data structures and recipe-related representations. Block Silo can function to transform recipes into data forms describing recipe characteristics (e.g., which recipes use which food items, etc.), where the data forms can be suitable for subsequent processing by other portions of the method 100 (e.g., determination of food substitutability for the food items of the recipes; etc.).

A recipe database preferably includes at least one of: recipe data structures, recipe-related representations, associations with users (e.g., recipe data structures and/or recipe-related representations personalized for and associated with a user, etc.), other suitable associations (e.g., with substitutable ingredient entities for a given recipe; with grocers capable of or incapable of fulfilling a food purchase plan including food items for a given recipe; with any suitable data types described herein; etc.) and/or any other suitable components. In a specific example, the recipe database can include, for each recipe: a recipe data structure describing characteristics of the recipe, a first recipe vector representation derived from the recipe data structure, and a second recipe vector representation describing ingredient entities included in the recipe data structure. However, the recipe database can be configured in any suitable manner (e.g., including any suitable combination of components describing any recipe characteristics).

Generating a recipe database preferably includes generating recipe data structures (e.g., a structure recipe, etc.) for recipes based on recipe characteristics (e.g., including recipe ingredients, amount, preparation steps, preparation level of ingredients, metadata such as difficulty of preparation, time of preparation, associated dietary characteristics such as gluten-free, vegetarian, vegan, ketogenic, dairy-free, low fat, low sugar, etc.). Recipe data structures can additionally or alternatively include and/or be associated with one or more media components (e.g., images, video, audio, graphics, emojis, augmented reality, virtual reality, etc.) describing one or more aspects of the recipe data structure (e.g., images of the ingredient entities of the recipe data structure, etc.). A recipe data structure preferably includes a title, an ingredient parameter set (e.g., ingredient lines, machine-learned parameters, etc.), and/or preparation parameters (e.g., describing preparation steps for the recipe), but can additionally or alternatively include any suitable parameters associated with recipe information for the recipe. An ingredient parameter set (e.g., of the recipe data structure) preferably includes (e.g., for each ingredient) the ingredient entity type (e.g., pepper, salt, salmon, kale, etc.), preparation level (e.g., partial preparation, such as skinless or skin-included salmon, diced or whole tomato, etc.), amount (e.g., in numerical values), and/or unit of measure (e.g., pounds, ounces, units of volume, etc.), but the ingredient parameter set can additionally or alternatively include any other suitable ingredient-related characteristics (e.g., seasonality parameters, diet-related parameters such as nutrition information, origin parameters such as indications of organic, place of origin, sustainability parameters, etc.).

Preparation parameters (e.g., of the recipe data structure) are preferably mapped to different sets of ingredient parameters corresponding to different ingredient entities (e.g., for a preparation step describing preparation of one or more ingredient entities, mapping a set of corresponding preparation parameters to one or more sets of ingredient parameters for the one or more ingredient entities, etc.). Mapping preparation parameters and/or otherwise associating preparation parameters to ingredients (e.g., ingredient parameter sets, etc.) is preferably based on a parsing of the preparation text (e.g., identifying references to ingredient entities in the preparation text) describing the preparation steps (e.g., classifying the preparation text into different types of preparation steps; deconstructing the preparation text into a preparation action such as "grill", a preparation time such as "5 minutes", etc.).

Additionally or alternatively, transforming preparation text into preparation parameters and/or otherwise generating preparation parameters for recipes can be performed in any suitable manner. For instance, a preparation action in text form can be converted to image form (e.g., as an icon, as an emoji, etc. automatically, using a translation matrix, etc.). In specific examples, text for "bake" can be converted to an emoji of an oven, text for "grill" can be converted to an emoji of a grill, text for "fry" can be converted to an emoji of a frying pan, etc. Generating preparation parameters can function to facilitate determination of food substitution parameters (e.g., inferring food substitutability based on processing preparation parameters across a plurality of recipes; etc.), facilitate recipe modification (e.g., modifying preparation steps presented to a user) in response to performing one or more food substitutions for ingredients in a recipe, and/or can have any other suitable functions. However, recipe data structures and/or associated components can be configured in any suitable manner.

Generating recipe data structures (e.g., ingredient parameter sets, preparation parameters, etc.) preferably includes applying a natural language approach (e.g., natural language processing algorithms, natural language understanding algorithms, etc.) to collected recipe information for recipes. Additionally or alternatively, generating recipe data structures can be performed using any suitable approaches described herein.

Block S110 preferably includes generating recipe-related representations based on the recipe data structures. Recipe-related representations preferably include a first recipe vector representation of one or more recipe data structures (e.g., determined in Block S110) and/or a second recipe vector representation of one or more ingredient entities (e.g., a vector representation of each ingredient entity in a given recipe, such as a recipe described by another vector representation for a corresponding recipe data structure, etc.), other ingredient parameters, preparation parameters, and/or other recipe characteristics (e.g., included in the recipe data structure; where the second recipe vector representation can facilitate determination and/or application of food substitution parameters for ingredient substitution; etc.), but can additionally or alternatively include any other suitable recipe-related representations in any suitable form (e.g., a non-vector form).

Vector representations of food-related data (e.g., recipe data structures, ingredients or ingredient entities, user food preferences, etc.) can function to enable comparison of such data (e.g., with like data, with similar data, with subsets of partially similar data, etc.) across a vector of data features. Vector representations can also function to enable representation of food-related data at various hierarchies (e.g., wherein a recipe can be represented by a recipe vector and define a set of ingredients that are each represented by an ingredient vector).

Vector representations of food related data can enable constraints to be applied in the vector space in which the food-related data is represented. For example, in determining a personalized food plan (e.g., as in Block 150), recipe vector representations can be compared to the constraints (e.g., elementwise constraints on the magnitude of components of the vector, norm-based constraints on the combined vector magnitude of the vector representation, etc.) to determine whether the recipe represented by the recipe vector satisfies the constraints of the personalized food plan. In another example, in determining substitution parameters (e.g., as in Block 120), ingredient vector representations can be compared to constraints (e.g., elementwise constraints on the magnitude of vector components, relative constraints on the distance of the vector from other ingredient vectors in one or more dimensions, etc.) to determine whether an ingredient is a suitable substitute for another ingredient. However, vector representations can be otherwise suitably used to make any other suitable comparison.

Vector representations of food-related data are preferably generated as a result of processing the food-related data at a trained synthetic neural network defining a plurality of neuronal layers. Such neural networks can be convolutional neural networks (CNNs), deep learning networks, and any other suitable configuration or representation of a linked set of numerical operations that process input data into output data in a vectorized manner. The vector representation of a food-related datum is preferably an intermediate layer of such a neural network, and thus represented by a set of weights (e.g., vector component values) defining a vector in a vector space spanning the domain of the neural network.

In variations, the method can include deriving a recipe vector representation of each of a set of recipe data structures, including: training a neural network model using each of the set of recipe data structures as inputs, wherein the neural network model is made up of a plurality of neuronal layers, and wherein the recipe vector representation is generated from (e.g., equivalent to) an intermediate layer (e.g., the weights associated with the intermediate layer) of the plurality of neuronal layers. Analogously, the method can include deriving a vector representation of any other suitable type of food-related data (e.g., ingredients, preparation parameters, user food preferences, etc.) described herein in a similar manner (e.g., using a different neural network model configured similarly but directed to solving a distinct problem, wherein the distinct problem is related to the food-related data type being represented; using an end-to-end model encompassing each suitable food-related data type, where a subset of the dimensions of the model correspond to a particular food-related data type; etc.).

Generating the recipe database (e.g., recipe data structures, recipe-related representations, other suitable components), determining other suitable outputs, and/or performing other suitable portions of the method 100 can include determining and/or applying one or more food-related models (e.g., recipe models, food substitution models, food plan models, etc.) and/or other approaches, where the models and/or other approaches can include any one or more of: probabilistic properties, heuristic properties, deterministic properties, and/or any other suitable properties. In variations, Block S110 and/or other suitable portions of the method 100 can employ machine learning approaches including any one or more of: semi-supervised learning, supervised learning (e.g., using logistic regression, using back propagation neural networks, using random forests, decision trees, etc.), unsupervised learning (e.g., using an Apriori algorithm, using K-means clustering), reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial least squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and/or any suitable form of machine learning algorithm.

In a specific example, Block S110 can include applying a deep neural network with a semi-supervised learning step in mapping recipe data structures intro corresponding recipe-related representations (e.g., recipe vector representations), but any suitable model can additionally or alternatively be applied. The models (and/or portions of the method 100) and/or other approaches can be universally applicable (e.g., the same models used across users, grocers, food items, recipes, food plans, etc.), specific to different entities and/or combinations of entities (e.g., different models for different subgroups of users sharing one or more user characteristics such as dietary preferences; different models for different food groupings; etc.), specific to different geographic regions (e.g., where user food preferences, fulfillment parameters, and/or other suitable parameters can differ based on geographic region, etc.), and/or can be applicable in any suitable manner.

Each model can be run, validated, verified, reinforced, calibrated, and/or updated: once; at a predetermined frequency; every time an instance of an embodiment and/or portion of the method 100 is performed, every time a trigger condition is satisfied (e.g., collecting additional recipe characteristic data for current and/or new recipes, receiving other new data, a user logging in, receiving updated fulfillment parameters, receiving user feedback, detection of unanticipated data; etc.), and/or at any other suitable time and frequency. Models can be run or updated concurrently with one or more other models, serially, at varying frequencies, and/or at any other suitable time. Each model can be validated, verified, reinforced, calibrated, or otherwise updated based on newly received, up-to-date data; historical data or be updated based on any other suitable data.

In variations, recipe characteristic data (e.g., upon which recipe data structures and/or recipe-related representations can be generated) and/or other suitable inputs can be obtained through one or more of: querying third party recipe databases, information scraping, recipe creation de novo, and/or any other suitable approaches. Additionally or alternatively, the inputs and/or features (e.g., parameters used in an equation, features used in a machine learning model, etc.) used in models and/or other approaches can be determined through a sensitivity analysis, used for a plurality of models, received from other models (e.g., outputs of other models), received from a user and/or grocer, automatically retrieved, extracted from sampled sensor data (e.g., from a connected food device, etc.), and/or otherwise determined. Additionally or alternatively, determining and/or applying food-related models and/or other suitable food-related approaches can be performed in any suitable manner. However, generating a recipe database can be performed in any suitable manner.

2.2 Determining Food Substitution Parameters.

Block S120 can include determining food substitution parameters based on the recipe database. Block S120 can function to facilitate food substitutions (e.g., ingredient substitutions) for recipes (e.g., for accommodating unavailability of an ingredient entity for a selected recipe; for accommodating user food preferences, such as dietary preferences requiring removal of an ingredient entity from a selected recipe; for accommodating user food allergies; for accommodating substitutions that allow a user to use an ingredient entity they already have available, etc.) and/or other suitable food-related components described herein.

Food substitution parameters can include any one or more of: ingredient entity substitutions, recipe substitutions, and/or substitutions at any suitable granularity for any suitable data types described herein. In an example, food substitution parameters can be associated with a probability that a health-related professional and/or other suitable entity (e.g., based on collected inputs by health-related professionals, which can be used as labels for training data in generating a food substitution model, etc.) would agree that the food substitution is appropriate (e.g., according to any suitable optimization parameters, including taste parameters, dietary parameters, cost parameters, environmental sustainability parameters, perishability parameters, convenience parameters, etc.).

Any number of ingredient entities and/or recipe-related components can be substituted (e.g., for a given recipe, any number of ingredient entities can be substituted with any number of substitute ingredient entities; etc.). In an example, food substitution parameters can indicate a food substitution of a single substitute ingredient entity in place of a plurality of ingredient entities and/or a food substitution of a partially prepared item (e.g., ingredient entity with a preparation step in a recipe to produce an alternative ingredient entity, partially-prepared ingredient entity provided by a food supplier), which could allow a reduction in required preparation time/effort. Food substitution parameters can be universally applicable (e.g., determined for different ingredient entities, and applicable across users, grocers, etc.), segmented (e.g., different food substitution parameters for a set of ingredient entities depending on a given user subgroup sharing one or more user food preferences; different food substitution parameters for different specific entities and/or combination of entities; etc.), and/or otherwise suitably applicable to ingredient entities.

In a variation, Block S120 can include determining different food substitution parameters based on optimization parameters. For example, different pairwise rankings can be determined based on different optimization parameters applied to the determination process (e.g., optimizing for similar taste to the original recipe, optimizing for ensuring dietary preferences are satisfied, optimizing for maintaining a final cost within a threshold of an initial estimated cost for the pre-substitution recipe; etc.).

Determining food substitution parameters can additionally or alternatively be based on one or more of: recipe database components (e.g., recipe-related representations, recipe data structures, etc.), health-related professional inputs (e.g., collected in Block S170), user inputs (e.g., user feedback, such as regarding how a user rates a recipe that included one or more food substitutions; user purchases, such as purchases for ingredient entities other than those presented in a personalized food plans, where such purchases can indicate a user-determined food substitution; etc.), and/or any other suitable data. In an example, one or more vector spaces can be determined based on recipe-related representations (e.g., from the recipe database), where food substitution parameters can be determined based on distance between different representations in the one or more vector spaces. In a specific example, Block S120 can include determining a pairwise ranking for different types of cheese, such as determining parmesan cheese as a viable food substitution (and/or other suitable ingredient entities as viable food substitutions, such as based on a ranking of food substitutions; etc.) for asiago cheese for one or more recipes, based on distance between recipe-related representations for parmesan cheese and asiago cheese in the vector space. Additionally or alternatively, Block S120 can include determining and/or applying one or more food substitution models (e.g., food ranking models) and/or other approaches (e.g., analogous to those described herein, such as in relation to food-related models, etc.). Block S120 can additionally or alternatively include generating a food substitution database (e.g., including stored pairwise rankings for different ingredient entities, etc.). However, determining food substitution parameters can be performed in any suitable manner.

2.3 Determining User Food Preferences.

Block S130 can include determining user food preferences, which can function to improve food-related personalization for a user according to associated preferences.

User food preferences can include any one or more of: grocery item preferences (e.g., organic versus non-organic, brands, current food items already owned by the user, etc.) and/or preferences for minimizing leftover ingredients (e.g., in relation to quantity purchased vs. quantity needed, in relation to minimizing cost per unit of an item, etc.), dietary preferences (e.g., vegan, keto, gluten-free, allergies, caloric preferences, macronutrient preferences, micronutrient preferences, etc.), taste preferences (e.g., types of cuisines, texture, types of tastes, preferences for sweetness, sourness, saltiness, bitterness, umami, etc.), cooking preferences (e.g., time to cook, difficulty, user skill level for cooking, serving size, cooking devices and/or other suitable tools involved, partially-prepared item selection, user preference for financial cost/time cost/efficiency cost tradeoffs, etc.), and/or any other suitable food-related preferences.

User food preferences can be determined and/or applied for food items (e.g., food preferences for different types of vegetables, etc.), recipes and/or meals (e.g., food preferences for a "steak and eggs" meal, etc.), and/or at any suitable granularity of food-related components. For example, dietary preferences (e.g., shellfish allergies) can be applied in selection of food items (e.g., avoidance of shrimp in determining a personalized food plan, etc.) as well as meals and recipes (e.g., avoidance of a "shrimp tacos" recipe). In another example, taste preferences can apply in selection of recipes, but omitted or applied with a lower weighting in determining food items. However, any suitable user food preferences can be applied in any suitable manner (e.g., with any suitable weighting) for determining any suitable food-related components (e.g., food substitutions, recipes, food items, grocery items, etc.).

Determining user food preferences is preferably based on user inputs. For example, Block S130 can include collecting user selections for different potential user food preferences presented to a user at an interface (e.g., web interface, mobile application interface, etc.). In another example, Block S130 can include inferring user food preferences based on user actions (e.g., user selections of recipes; user-determined food substitutions; etc.). In another example, Block S130 can include extracting user food preferences from third party databases (e.g., grocer databases, food delivery services databases, social media databases, etc.). In another example, Block S130 can include inferring user food preferences based on food device data (e.g., based on classification data describing food items cooked by a connected food device, etc.). In another example, Block S130 can include inferring user food preferences based on user characteristics (e.g., demographic information, geographic location, etc.). Additionally or alternatively, user food preferences can be determined with a user food preference model and/or other suitable approach (e.g., described herein) based on any suitable types of data.

In a variation, determining user food preferences can include generating a user food preferences database (e.g., associating user food preferences with user identifiers such as user account handles, recipe database components, other suitable data, etc.). However, determining user food preferences can be performed in any suitable manner.

2.4 Determining Fulfillment Parameters.

Block S140 can include determining fulfillment parameters for grocery items associated with the food-related personalization. Block S140 can function to inform purchase and/or delivery of food items for personalized food plans and/or other suitable food-related components.

Fulfillment parameters can include one or more of: availability parameters (e.g., quantity available, availability of food substitutes, etc.), location parameters (e.g., location of associated grocer, distance from a given user, etc.), cost parameters (e.g., actual cost, estimated cost such as based on historical cost parameters and/or other suitable parameters for a food item, etc.), grocer parameters (e.g., type of grocer, available purchasing options, available pickup options, etc.), grocery item parameters (e.g., grocery item data structures and/or other suitable representations of grocery items; representations sharing components included in recipe data structures and/or recipe-related representations, such as preparation levels, vector representation forms, etc.), delivery parameters (e.g., estimated time for delivery from a fulfillment source, associated delivery services, parking conditions proximal the grocer, etc.), food substitution-associated parameters (e.g., in relation to partially prepared items, as described above), and/or any other suitable parameters associated with fulfillment. In a specific example, fulfillment parameters can include a probabilistic estimate of item fulfillment (e.g., of likeliness that a selected item, some subset, or all items can be fulfilled, such as for a specific grocer, etc.).

Fulfillment parameters are preferably determined based on grocer data (e.g., indicating inventory, prices, user purchase history, etc.). In examples, grocer data can be collected through third party databases (e.g., through API requests to grocer databases, etc.), information scraping (e.g., of grocer online websites, based on processing a URL of a grocery item listed on a grocer's online store, based on processing a JSON file that can be extracted from a server associated with the grocer's online store, etc.), manual inputs (e.g., by food purchasers of food items included in a personalized food plan, by users fulfilling a personalized food plan, by employees and/or other entities associated with a grocery, etc.), and/or through any other suitable approach. In a variation, determining fulfillment parameters can include generating a fulfillment database (e.g., storing fulfillment parameters in association with grocer identifiers, etc.). However, determining fulfillment parameters can be performed in any suitable manner.

2.5 Determining a Personalized Food Plan.

Block S150 can include determining one or more personalized food plans for a user based on at least one of user food preferences, fulfillment parameters (e.g., in relation to ingredient availability, in relation to ingredient delivery, etc.), food substitution parameters, recipe-related representations, and recipe data structures, where the one or more food personalized food plans can facilitate physical delivery of the food items corresponding to the personalized food plans. Block S150 can function to output personalized food-related components for one or more users.

Personalized food plans can include any one or more of: food purchase plans (e.g., a list of grocery items to purchase, where the grocery items can correspond to ingredients included in a recommended recipe, etc.), personalized recipes (e.g., modified recipes, generated recipes, etc.), health recommendations (e.g., dietary behavior recommendations, physical activity recommendations, etc.), food-related device parameters (e.g., control instructions for a cooking device to cook a personalized meal based on personalized recipes and/or components of the food purchase plan, etc.), and/or any other suitable personalized food-related components. Food purchase plans can include any one or more of: different ingredient parameters (e.g., ingredient entities, preparation levels, amounts, units of measure, etc.), associated price parameters (e.g., price for a particular ingredient entity at a particular amount and unit of measure, etc.), associated grocer parameters (e.g., grocers capable of fulfilling items of the food purchase plans, etc.), associated delivery parameters, etc.), and/or any other suitable parameters associated with purchase, delivery, and/or other fulfillment-related aspects.

Determining personalized food plans can be based on one or more of: user food preferences (e.g., selecting food items and/or recipes satisfying dietary restrictions; selecting recipes matching taste preferences; etc.), fulfillment parameters (e.g., generating a food purchase plan based on matching grocery items to ingredient entities included in a personalized recipe for a user; selecting recipes based on capability of satisfying fulfillment parameters such as availability and/or time for delivery; selecting recipes based on likelihood of being fulfilled and/or an estimated price; etc.), food substitution parameters (e.g., modifying an ingredient entity of recommended recipe by using food substitution parameters and user food preference parameters to select a substitute ingredient entity that results in a similar taste to the original recipe while satisfying dietary preferences of the user; modifying preparation parameters of a recommended recipe based on applied food substitutions; etc.), recipe data structures, recipe-related representations (e.g., from which recommended recipes can be selected and/or modified, etc.), and/or any other suitable data.

Determining personalized food plans preferably includes applying one or more food plan models (e.g., including any suitable properties and/or algorithms described herein, such as in relation to food-related models, etc.), but can additionally or alternatively include applying any other suitable approaches. For example, Block S150 can include applying a food plan model to determine pairwise rankings of grocery items matching against recipe ingredients (e.g., components of recipe data structures and/or recipe-related representations), such as for determining fulfillment capability for different recipes, recipe ingredients, and/or other suitable food-related components. In another example, Block S150 can include applying a semi-supervised training approach for generating a food plan model (e.g., wherein supervision is manually performed by a human entity, automatically performed using a bot or machine learning technique, etc.), where health-related professionals and/or other suitable entities (e.g., users, etc.) can provide selections of personalized food plans (e.g., recipe recommendations) in the context of different user food preferences, fulfillment parameters, and/or food substitution parameters. In another example, Block S150 can include applying a deep neural network with at least one of user food preferences, fulfillment parameters, food substitution parameters, recipe-related representations, recipe data structures, and/or other suitable data in outputting one or more components of personalized food plans.

In a variation, Block S150 can include determining any suitable number and/or type of personalized food plans (e.g., including any combination of personalized food plan components, etc.). In an example, Block S150 can include determining a plurality of personalized purchase plans satisfying parameters (e.g., user food preferences, fulfillment parameters, etc.); ranking the personalized purchase plans (e.g., based on satisfaction of optimization parameters, such as optimization parameters selected by and/or inferred for a user; etc.); and presenting the ranked personalized purchase plans to a user. In a specific example, ranked personalized food plans (e.g., including grocery item dependencies, etc.) can be transmitted to a food purchaser (e.g., for purchasing food items in-store and/or online, etc.) who can select grocery items to purchase based on the ranked personalized food plans. In another specific example, ranked personalized purchase plans can be transmitted to a health-related professional who can provide related inputs (e.g., modified rankings; selections of personalized food plans; inputs for facilitating semi-supervised learning; etc.).

In another variation, Block S150 can include determining a modified recipe based on a food purchase plan (e.g., fulfillment status of a food purchase plan, such as a comparison between food items purchased and food items recommended to be purchased in the food purchase plan, etc.) and/or an original recipe (e.g., an initially recommended recipe, a recipe corresponding to a stored recipe database component, etc.), such as where the modified recipe can include one or more of: a recipe with one or more food substitutions for the associated ingredient entities, a different recipe (e.g., corresponding to a stored recipe database component with ingredient entities matching the purchased food items, etc.), and/or other suitable components. However, determining personalized food plans can be performed in any suitable manner.

2.6 Updating Components Associated with the Food-Related Personalization.

Block S160 can include updating components associated with the food-related personalization (e.g., food-related models, food substitution parameters such as pairwise rankings for food substitutability, user food preferences, etc.) and/or other suitable data described herein S160. Block S160 can function to update food-related components based on additional data (e.g., newly received data, etc.) in order to improve food personalization (e.g., personalized food plans, personalized recipe recommendations, and/or other food-related components, etc.).

Updating food-related components can be based on one or more of: user feedback (e.g., ratings for recommended recipes; ratings for food substitutions; etc.), user actions (e.g., conversion rate from presentation of food items in a personalized food plan to purchase of the same food items, user actions in relation to user food preferences, application usage such as tracked taps and selections, purchasing behavior, recipe selection behavior, any suitable behaviors associated with the food-related components, etc.), goals (e.g., dietary goals, goal setting behaviors, goal meeting behaviors, etc.), health-related professional actions (e.g., health-related professional inputs for food substitutability, etc.), grocer-related actions (e.g., fulfillment trends, grocer behaviors, etc.), and/or any other suitable data.

Updating food-related components is preferably performed at a remote computing system (e.g., storing food-related models, other food-related components, etc.), but can be performed at any suitable system. However, updating food-related components can be performed in any suitable manner.

2.7 Processing Recipe-Related Inputs.

The method 100 can additionally or alternatively include Block Silo, which can include processing recipe-related inputs from one or more health-related professionals (e.g., nutritionist, dietician, food expert, chef, physical trainer, other subject matter experts or SMEs, etc.). Block Silo can function to improve food-related models and/or other suitable approaches described herein.

Recipe-related inputs can include any one or more of: feedback for food substitution parameters, references (e.g., supporting food substitution parameter selections by the health-related professionals), food plan parameters (e.g., selections of recipes recommended according to different user food preferences, food substitution parameters, and/or other suitable parameters, etc.), and/or any other suitable recipe-related inputs related to any suitable food-related components.

In an example, processing recipe-related inputs could include providing an interface for health-related professionals, such as where health-related professionals can provide the recipe-related inputs at the interface. In a specific example, processing recipe-related inputs can include presenting a recipe (e.g., ingredient entities for a recipe) and potential food substitutions (e.g., provided by a food substitution model; for any ingredient parameter set corresponding to a recipe ingredient; a ranked ordered list of substitutions); and collecting recipe-related inputs (e.g., a modified ranking of food substitutions for an ingredient entity of a recipe, etc.). In another example, processing recipe-related inputs can include collecting recipe-related inputs for different optimization parameters (e.g., prompting health-related professionals to select suitable food substitutions for optimizing taste, dietary preferences, cost, etc.). In another example, recipe-related inputs can be associated with grocery items and/or grocers (e.g., selecting food substitutions with specific grocery items sold at a grocer, etc.). However, processing recipe-related inputs can be performed in any suitable manner.

Although omitted for conciseness, the preferred embodiments include every combination and permutation of the various system components and the various method processes, including any variations, examples, and specific examples, where the method processes can be performed in any suitable order, sequentially or concurrently.

The system and method and variations thereof can be embodied and/or implemented at least in part as a machine configured to receive a computer-readable medium storing computer-readable instructions. The instructions are preferably executed by computer-executable components preferably integrated with the system.

The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

We claim:

1. A method for improving food-related personalization for a user, comprising:
   determining a set of recipe data structures from a set of recipes, comprising: parsing each recipe into a preparation parameter set and an ingredient entity set, identifying references to ingredient entities of the ingredient entity set in the preparation parameters of the preparation parameter set, and mapping the preparation parameters and the respective ingredient entities together, wherein a recipe data structure is modified with a substitute instruction based on the mapping;
   deriving a recipe vector representation of each of the set of recipe data structures, comprising using a trained neural network model to determine the recipe vector representation comprising values equivalent to a set of weights of an intermediate layer of the trained neural network model;
   deriving an ingredient vector representation associated with each ingredient entity of the set of ingredient entities using the trained neural network model;
   determining a set of substitution parameters associated with each ingredient entity of the set of ingredient entities based on the ingredient vector representation, comprising comparing the ingredient vector representation of each ingredient entity with the ingredient vector representation of each other ingredient entity;
   determining a set of user food preferences; and
   determining a personalized food plan based on the recipe vector representation of each of the set of recipe data structures and the set of user food preferences.

2. The method of claim 1, wherein the set of recipe data structures comprises natural language data.

3. The method of claim 1, wherein the neural network model is trained using semi-supervised learning.

4. The method of claim 1, wherein the set of user food preferences are determined at least in part based on social media content.

5. The method of claim 1, wherein the set of user food preferences comprises a user allergy.

6. The method of claim 1, further comprising determining a constraint associated with the set of user food preferences, wherein determining the personalized food plan comprises:
comparing the recipe vector representation of each of the set of recipe data structures to the constraint; and
selecting recipe data structures of the set of recipe data structures that satisfy the constraint based on the comparison.

7. The method of claim 6, wherein the constraint is an item availability constraint.

8. The method of claim 1, further comprising automatically facilitating fulfillment of grocery items associated with the personalized food plan.

9. The method of claim 8, wherein automatically facilitating fulfillment of grocery items comprises facilitating physical transport of the grocery items.

10. The method of claim 1, further comprising determining fulfilled items, and updating the personalized food plan based on the fulfilled items.

11. A method for improving food-related personalization for a user, comprising:
determining a recipe data structure based on recipe data, comprising: parsing the recipe data into a preparation parameter set and an ingredient entity set, identifying references to ingredient entities of the ingredient entity set in the preparation parameters of the preparation parameter set, and mapping the preparation parameters to the respective ingredient entities;
deriving a recipe vector representation of the recipe data structure, including using a trained neural network model to determine the recipe vector representation having values equivalent to a set of weights of an intermediate layer of the trained neural network model;
determining a recipe vector constraint associated with the recipe data structure;
determining a first ingredient vector representation of a first ingredient entity of the set of ingredient entities and a second ingredient vector representation of a second ingredient entity of the set of ingredient entities, using the trained neural network model;
determining that the second ingredient entity can be substituted for the first ingredient including: comparing the second ingredient vector representation to the recipe vector constraint and based on the comparison, determining that the second ingredient vector satisfies the recipe vector constraint; and
generating a personalized food plan based on a comparison between the recipe vector constraint and the recipe vector representation.

12. The method of claim 11, wherein the trained neural network model comprises a plurality of neuronal layers and wherein the recipe vector representation comprises an intermediate layer of the plurality of neuronal layers.

13. The method of claim 11, wherein the recipe data structure is associated with the set of ingredient entities of a plurality of ingredient entities.

14. The method of claim 11, further comprising modifying a preparation parameter of the set of preparation parameters based on a modification to the set of ingredient entities associated with the recipe data structure.

15. The method of claim 14, wherein a connected cooking device is controlled according to the preparation parameter subsequent to modifying the preparation parameter.

16. A method for improving food-related personalization for a user, comprising:
determining a set of recipe data structures from a set of recipes, comprising: parsing each recipe into a preparation parameter set and an ingredient entity set, identifying references to ingredient entities of the ingredient entity set in the preparation parameters of the preparation parameter set, and mapping the preparation parameters and the respective ingredient entities together, wherein a recipe data structure is modified with a substitute instruction based on the mapping;
deriving a recipe vector representation of each of the set of recipe data structures, including using a trained neural network model to determine the recipe vector representation including values equivalent to a set of weights of an intermediate layer of the trained neural network model;
selecting a substitute ingredient entity for an ingredient entity of the ingredient entity set based on a probability that a food professional would agree that the substitute ingredient entity is an admissible substitute for the ingredient entity; wherein the probability is calculated based on a ranking of substitute ingredients by food professionals;
determining a set of user food preferences; and
determining a personalized food plan based on the recipe vector representation of each of the set of recipe data structures and the set of user food preferences.

* * * * *